(12) United States Patent
Mammone et al.

(10) Patent No.: US 6,531,140 B2
(45) Date of Patent: Mar. 11, 2003

(54) ANTI-IRRITANT COMPOSITIONS CONTAINING A CYCLIC NUCLEOTIDE

(75) Inventors: Thomas Mammone, Farmingdale, NY (US); Earl C. Goyarts, Commack, NY (US); Neelam Muizzuddin, Bethpage, NY (US)

(73) Assignee: E-L Management, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/304,562

(22) Filed: May 4, 1999

(65) Prior Publication Data

US 2002/0090384 A1 Jul. 11, 2002

(51) Int. Cl.⁷ .............................. A61K 6/00; A61K 7/00
(52) U.S. Cl. .......................... 424/401; 424/400; 424/47
(58) Field of Search ................................. 424/400, 401, 424/47; 536/26.1

(56) References Cited

U.S. PATENT DOCUMENTS 3,798,213 A  3/1974  Lapinet et al.
4,208,406 A  6/1980  Lapinet et al.

OTHER PUBLICATIONS

Helfman, D. M., et al., "Differential Effects of Various Phosphodiesterase Inhibitors, Pyrimidine and Purine Compounds, and Inorganic Phosphates on Cyclic CMP, Cyclic AMP and Cyclic GMP Phosphodiesterases", Biochemical Pharmacology, vol. 31, No. 1, pp. 43–47 (1982).
Hanifin, J. M., et al., "Type 4 Phosphodiesterase Inhibitors Have Clinical and In Vitro Anti–inflammatory Effects in Atopic Dermatitis", The Journal of Investigative Dermatology, vol. 104, No. 1, pp. 51–56 (1996).
Posternak, "Cyclic AMP and the Skin", Front. Matrix Biol., vol. 6 pp. 85–100 (1978).
Posternak, T., "Cyclic AMP and Cyclic GMP", Annu. Rev. Pharmacol., vol. 14, pp. 23–33 (1974).
Robison, G. A. et al., "Cyclic AMP", Chapter 1–5, pp. 1–145 (Academic, New York 1971).
Goyarts, E., et al., "Correlation Between In Vitro Cyclic Adenosine Monophosphate Phosphodiesterase Inhibition and In Vivo Anti–Inflammatory Effect", Skin Pharmacol Appl Skin Physiol, vol. 13, issue 2, pp. 86–92 (Mar., 2000).

*Primary Examiner*—Dameron L. Jones
(74) *Attorney, Agent, or Firm*—Darene M. Price, Esq.

(57) ABSTRACT

The present invention relates to cosmetic or pharmaceutical topical compositions containing at least one cyclic nucleotide having its 2' hydroxyl group replaced by a hydrogen atom for inhibiting phosphodiesterase activity. The phosphodiesterase inhibitor is in combination with a magnesium buffer and a cosmetically or pharmaceutically acceptable carrier. The invention also includes methods for treating or preventing inflammation or irritation such as is common in the skin disease, atopic dermatitis, which is known to be related to the uncontrolled activity of phosphodiesterase.

14 Claims, No Drawings

ANTI-IRRITANT COMPOSITIONS CONTAINING A CYCLIC NUCLEOTIDE

FIELD OF THE INVENTION

The present invention relates to topical anti-irritant compositions which contain a phosphodiesterase inhibitor. In particular, the invention relates to topical skin care compositions containing 2'-deoxy adenosine 3 '5' cyclic monophosphate which exhibit inhibitory action toward phosphodiesterase.

BACKGROUND OF THE INVENTION

Irritation and inflammation are complex processes that involve various factors such as, for example, prostaglandins, leukotrines, cytokines, proteases. Another factor is the intracellular level of cyclic adenosine monophosphate (hereinafter referred to as "cAMP"), and therefore, it is possible to control inflammation and irritation by modulating the levels of cAMP. Modulation can be achieved by employing one of two methods. One method involves the inhibition of new cAMP synthesis and the other method entails the removal of existing cAMP. One known removal method involves the use of an enzyme, cyclic nucleotide phosphodiesterase (hereinafter referred to as "PDE"). This isoenzyme is the catalyst for the hydrolytic reaction whereby cAMP is converted to adenosine 5' monophosphate (hereinafter referred to as "AMP"). A family of isoenyzmes is formed by various PDEs and is categorized into seven types, known as Types I–VII whereby the type is determined by the inhibitor sensitivity. Human epidermal keratinocytes have been shown to contain both Type IV and Type V phosphodiesterase activity.

As a result of its relationship with cAMP, it is also known in the prior art that PDE plays a role in inflammatory response. There is an abnormal elevated activity of PDE in leukocytes of patients with skin disorders such as atopic dermatitis. The presence of elevated PDE activity causes a deficiency in cAMP control and results in exaggerated immune and inflammatory responses in the blood and tissue. Since elevated PDE activity is known to have a correlation with irritation and inflammation, means of inhibiting PDE activity have, therefore, been sought.

PDE inhibitors have been shown to reduce the inflammation associated with atopic dermatitis. For example, there are "classical" inhibitors of PDE such as methylxanthines like caffeine, pentoxifylline and theophylline, and theobromine. However, methylxanthines may also exhibit numerous pharmacological activities which do not directly inhibit phosphodiesterase. Other active inhibitors include alkaloids, papaverine, and imidazolone derivatives, which are among the most potent PDE inhibitors known. Cosmetic use of cAMP and PDE inhibitors has been disclosed in U.S. Pat. No. 3,978,213. However, the presence of cAMP is not disclosed as a PDE inhibitor, and derivatives or analogs of cAMP are not disclosed as having any particular ability to inhibit PDE.

It has been recognized in recent years that 2'-deoxy cAMP and 2'-deoxy cGMP are specific and potent in vitro inhibitors of cAMP-PDE and cGMP-PDE, respectively. Helfman, D. M., et al., *Biochemical Pharmacology*, vol. 31, no. 1, pp. 43–47 (1982). Further, 2'-deoxy cyclic UMP may also be a specific PDE inhibitor. Id. In addition, a type IV PDE inhibitor CP80,633 has been tested in vivo and has been found to demonstrate a significant reduction of inflammatory parameters. Hanifin, J. M., et al., "Type 4 Phosphodiesterase Inhibitors Have Clinical and In Vitro Anti-inflammatory Effects in Atopic Dermatitis", The Journal of Investigative Dermatology, vol 104, no. 1, pgs. 51–56 (1996). The PDE inhibitors in this study are enantiomeric and racemic compounds and it is not disclosed in this study that topical application of 2'-deoxy cAMP exhibits inhibitory action toward PDE. Therefore, the ability of 2'-deoxy cAMP compounds to inhibit PDE when formulated in a topical cosmetic or pharmaceutical composition has not, until now, been demonstrated. The present invention now provides such a topical composition.

SUMMARY OF THE INVENTION

It has now been discovered that a topical cosmetic or pharmaceutical composition containing a cyclic nucleotide PDE inhibitor has effective anti-inflammation and/or anti-irritation properties when applied to the skin. The present invention thus relates to cosmetic or pharmaceutical topical compositions comprising a cyclic nucleotide having a 2' hydroxyl group replaced by a hydrogen atom as the phosphodiesterase inhibitor in combination with a cosmetically or pharmaceutically acceptable carrier. The invention also relates to a methods for treating or preventing symptoms of inflammation or irritation caused, in whole or in part by phosphodiesterase activity, as found in atopic dermatitis, by applying to the skin the compositions of the present invention.

DETAILED DESCRIPTION OF THE INVENTION

Cells contain the enzyme, phosphodiesterase (hereinafter referred to as "PDE"). A hydrolytic reaction which converts cyclic nucleotides into their corresponding non-cyclic nucleotide structure is catalyzed by PDE by specifically attacking the 3'-phosphoester or P-O(3') bond. Cyclic nucleotides are produced by the action of adenylate cyclase, which can be activated or inhibited to increase or decrease the steady state cAMP concentration. "Cyclic AMP and the Skin", *Front. Matrix Biol.*, vol. 6, pgs. 85–100 (1978). Cyclic nucleotides such as cAMP are major second messengers which mediate biological responses elicited by a vast number of extracellular signals. This requires a transport of exogenous cAMP into the cytoplasm of the cell. As a strong acid having a pK of 3.80, cAMP is completely dissociated under biological conditions. Further, it is commonly known that diffusion through the cell membrane of a phospho-organic anion is challenging and therefore, exogenous cAMP is known to have a weak action on intact cells. Therefore, synthetic analogs of cAMP, such as 2'-deoxy cAMP, have been prepared and studied to either better penetrate the cell membrane or to have better resistance to the action of PDE. Id., pp. 96–97, Posternak, "Cyclic AMP and Cyclic GMP", Annu. Rev. Pharmacol., vol. 14, pp. 23–33, 28 (1974). In general, synthetic compounds of cAMP have been found to be less active than exogenous cAMP, but they have also been found to be more active when applied to intact tissues. Robison, et al., *Cyclic AMP*, Chapter 5 "Some Actions of Cyclic AMP", p. 98 (Academic, New York 1971). The 2' hydroxyl (—OH) group is one of the reactive functions of cAMP that is capable of being transformed. Id., Chapter 3 "Chemistry of Cyclic Nucleotide Phosphates", pp. 64. Through such research, it became known that the hydrophobic and obstructing group in the 2' position of the ribose considerably hinders the action of PDE. However, the free hydroxyl (—OH) group in the 2' position is not considered to participate in the breakage of the phosphodiester bond, nor in the attachment to the active site of PDE as greater hydrolysis of 2'-deoxy cAMP than cAMP was found. Id.

It has now been surprisingly discovered that topically applied cosmetic or pharmaceutical compositions comprising a phosphodiesterase inhibitor in the form of a cyclic nucleotide having its 2' hydroxyl group (—OH) replaced by a hydrogen atom have anti-inflammatory and anti-irritating activities on the skin. The effects of cAMP are not consistent in all tissues. Chapter 5 "Some Actions of Cyclic AMP" pp. 92. Different derivatives and analogs of cAMP have varying abilities, if any at all, to inhibit PDE. Therefore, it is surprising to discover that a topical cosmetic or pharmaceutical composition can be prepared comprising a 2'-deoxy cyclic nucleotide as a PDE inhibitor.

In a typical formulation, the PDE inhibitor is present in a PDE inhibiting amount. As used in the present context, an "inhibiting amount" of the inhibitor is an amount which is sufficient to function as an anti-inflammatory or an anti-irritant by inhibiting PDE activity. Exemplary amounts are concentrations of from about 0.01 to about 10.00 percent by weight of the composition. Preferably, the concentration is about 0.1 to about 5.0 percent and more preferably, the concentration is about 0.5 to about 2.0 percent.

The cyclic nucleotide can be selected from 2'-deoxy cAMP, 2'-deoxy cGMP, and any other similar analog of 2'-deoxy cyclic nucleotide which inhibits PDE. Preferably, however, the cyclic nucleotide is 2'-deoxy cAMP which is available commercially in powder form Sigma Aldrich, St. Louis, Mo. Further, the inhibition of PDE can effect other related isoenzymes such as for example, cAMP PDE, and cGMP PDE. Accordingly, it is preferable that the compositions of the present invention have PDE type IV and type V inhibiting activity. Human epidermal keratinocytes are known to contain both type IV and type V phosphodiesterase activity. PDEs are classified into seven types of families (PDE I through VII) based on their different substrate specificities and sensitivities to activators and inhibitors.

Most families contain distinct genes and many of these genes are expressed in different tissues as functionally unique alternative splice variants. All PDEs have a core of about 270 amino acids in the COOH-terminal half of the protein. The PDEs within each of the seven families display about 65% amino acid homology. Most PDE genes have more than one alternatively spliced mRNA transcribed from them and in many cases the alternative splicing appears to be highly tissue specific providing a mechanism for selective expression of different PDEs. Cell type specific expression suggests that the different isoenzymes are likely to have different cell type specific properties. Type IV PDEs are the majority type of isoenzyme in inflammatory cells, and type V PDEs have been regarded as regulators of cGMP function but may also affect cAMP function as well.

The methods for formulating cosmetic or pharmaceutical compositions involve adding 2'-deoxy cAMP to cosmetic or pharmaceutical vehicles in which it is soluble. Therefore, it can be incorporated into a buffer solution containing, for example, magnesium, calcium, sodium, potassium, zinc, chlorine, or the like, a hydroalcohol such as for example ethanol, an aqueous vehicle, or the aqueous phase of a water-in-oil or oil-in-water emulsion. Given these guidelines, the 2'-deoxy cAMP PDE inhibitor can be incorporated into any type of vehicle which is acceptable for topical application; typical vehicles employed are lotions, creams, and sprays. It will be apparent to one of ordinary skill in the art how to choose an appropriate formulation for the particular use contemplated in accordance with the teachings of the present invention. Methods for formulation are known in the art, as shown for example, in Remington's "The Science and Practice of Pharmacy", 19th Ed., vol. II.

As a potent anti-inflammatory or anti-irritant, the compositions of the present invention have a number of uses in both cosmetic and therapeutic topical applications for treatment of irritation caused by UV radiation, psoriasis, eczema, atopic dermatitis, contact dermatitis, and the like. Further, the PDE inhibiting compositions can be employed in PDE inhibiting effective amounts as a sole active ingredient in a cosmetic or pharmaceutical topical composition intended for treatment or prevention of skin irritation or inflammation which occurs as the result of increased PDE activity. Alternatively, the 2'-deoxy cAMP PDE inhibitor can also be used in combination with other anti-irritants or anti-inflammatories known by one of ordinary skill in the art. In this context, either alone or in combination, the 2'-deoxy cAMP PDE inhibitors can be added to makeup, such as foundation, blush, eyeshadow, lipstick, and to skin treatment products, such as moisturizers, lip balms, eye creams, and the like.

In a related embodiment, 2'-deoxy cAMP PDE inhibitors of the present invention can also be used in compositions that contain ingredients to which certain individuals in the general population may have be sensitive, although the ingredient itself may not be regarded as irritating in general. For this purpose, the 2'-deoxy cAMP PDE inhibitor can be used in combination with other active ingredients, as for example, alpha-hydroxyacids such as lactic acid, glycolic acid, citric acid, alpha-hydroxyoctanoic acid, alpha-hydroxydecanoic acid, alpha-hydroxylauric acid, tartaric acid, glucouronic acid, galactouronic acid, alpha-hydroxybutyric acid, alpha-hydroxyisobutyric acid, malic acid, mandelic acid, pyruvic acid, and tartronic acid, alpha-hydroxydecanoic and alpha-hydroxyoctanoic acids; and beta-hydroxyacids such as salicylic acid, retinoids such as retinol (Vitamin A), retinoic acid (Vitamin A acid), retinal (Vitamin A aldehyde), and retinoic acid esters or amides, e.g., retinyl palmitate or retinyl acetate. The PDE inhibitors containing compositions of the present invention may also be combined with any other active ingredient. In any such combined composition, each active component is used in the amounts standard in the art for the treatment of symptoms related to the active component.

The following non-limiting examples further illustrate the invention.

EXAMPLES

Example 1

Study of Various Concentrations of 2'-deoxy cAMP

Eight female volunteer panelists between the ages of 21 and 55 having a history of skin sensitivity to Balsam of Peru are chosen for a study. Those selected are in normal health and do not exhibit any evidence of acute or chronic disease including dermatological or ophthalmologic problems. The panelists have a history of skin reactivity to Balsam of Peru which manifests itself in the form of an immediate urticaria reaction. The test sites on the ventral forearms of the panelists are devoid of warts, nevi, moles, sunburn, suntan, scars and active dermal lesions. Pregnant or lactating volunteers are excluded. The compositions prepared according the present invention at concentrations of 0.05, 0.25, and 0.50 percent in magnesium buffer are applied on the ventral forearms of each of the panelists. The composition is given time, about 20 minutes, to absorb into the skin on the forearm. Next, an irritant, Balsam of Peru, 8.00 percent in petrolatum, is applied to the test area of the skin and when redness appears within 30 to 40 minutes after application, Balsam of Peru is wiped off with a wet towel. Skin redness is measured with the Minolta Chromameter.

Skin irritation is measured in terms of an increase in skin redness measured using a Minolta Chromameter and compared with a negative and a positive control. The positive control is the color of the skin treated solely with Balsam of Peru, and the negative control is the color of the skin treated with a cola nitida solution in 10% hydroalcohol (1:1).

Results. Using the composition of the present invention comprising 2'-deoxy cAMP at a concentration of 0.5 percent, a 74% reduction in the onset of irritation is observed thereby indicating that 2'-deoxy cAMP exhibits excellent anti-irritancy activity.

Example 2

Comparison of 2'-deoxy cAMP with other PDE Inhibitors

Compounds containing 2'-deoxy cAMP at 0.5% and compounds containing the following PDE inhibitors, Rolipram, 3-isobutyl 1-methyl xanthine ("IBMX"), Ro-20-1724, pentoxifylline, caffeine, and cyclic IMP, are each prepared at 1% concentration and administered as described above. The results are measured in % inhibition of irritation and are provided in Table 1 below. At a 0.5% concentration, 2'-deoxy cAMP exhibits the greatest % reduction in the onset of irritation at 71%.

TABLE 1

| PDE Inhibitors | Percent Reduction in the onset of irritation |
|---|---|
| 2'-deoxy cAMP | 71 |
| Rolipram | 69 |
| IBMX | 66 |
| Ro-12-1724 | 57 |
| Pentoxifylline | 50 |
| Caffeine | 45 |
| cIMP | 42 |

What we claim is:

1. A cosmetic or pharmaceutical topical composition comprising a phosphodiesterase inhibitor comprising a cyclic nucleotide having a 2' hydroxyl group replaced by a hydrogen atom in combination with a cosmetically or pharmaceutically acceptable carrier.

2. The composition of claim 1 wherein said inhibitor is present in a phosphodiesterase inhibiting amount.

3. The composition of claim 2 wherein said inhibitor is a Type IV phosphodiesterase inhibitor.

4. The composition of claim 2 wherein said inhibitor is a Type V phosphodiesterase inhibitor.

5. The composition of claim 2 wherein said inhibitor is selected from the group consisting of 2'-deoxy cyclic AMP, 2'-deoxy cyclic GMP, and 2'-deoxy cyclic UMP.

6. The composition of claim 5 wherein said inhibitor is 2'-deoxy cyclic AMP.

7. The composition of claim 6 wherein said inhibitor is present at a concentration of from about 0.01 to about 10.00 weight percent of the composition.

8. The composition of claim 7 wherein said inhibitor is present at a concentration of from about 0.5 to about 5.0 percent.

9. The composition of claim 8 wherein said inhibitor is present at a concentration of about 0.5 to 2.0 percent.

10. The composition of claim 1 further comprising an active ingredient.

11. A method for treating or reducing symptoms of inflammation or irritation, which comprises applying to the skin an effective amount of the composition of claim 1.

12. A method for treating inflammation or irritation caused, in whole or in part, by phosphodiesterase activity comprising applying to the skin a therapeutically effective amount of the composition of claim 1.

13. The method of claim 12 comprising applying the composition wherein said inhibitor is 2'-deoxy cyclic AMP.

14. A method of treating atopic dermatitis comprising applying to the skin a cosmetic or pharmaceutical composition which comprises a phosphodiesterase inhibitor being present at a concentration of about 0.5 to about 2.0 percent and comprising a cyclic nucleotide having a 2' hydroxyl group replaced by a hydrogen atom in combination with a cosmetically or pharmaceutically acceptable carrier.

* * * * *